(12) United States Patent
Hoang et al.

(10) Patent No.: US 12,706,487 B2
(45) Date of Patent: Aug. 11, 2026

(54) IMPLANTABLE MEDICAL DEVICE AND METHOD TO MANUFACTURE SUCH A DEVICE

(71) Applicant: VERMON SA, Tours (FR)

(72) Inventors: Thien Hoang, Tours (FR); Bogdan Rosinski, Tours (FR); Nicolas Felix, Tours (FR)

(73) Assignee: VERMON SA, Tours (FR)

( * ) Notice: Subject to any disclaimer, the term of this patent is extended or adjusted under 35 U.S.C. 154(b) by 115 days.

(21) Appl. No.: 18/342,094

(22) Filed: Jun. 27, 2023

(65) Prior Publication Data

US 2023/0420995 A1 Dec. 28, 2023

(30) Foreign Application Priority Data

Jun. 28, 2022 (FR) ..................................... 22/06419

(51) Int. Cl.
*H02J 50/15* (2016.01)
*B06B 1/06* (2006.01)
*A61N 1/378* (2006.01)

(52) U.S. Cl.
CPC ................ *H02J 50/15* (2016.02); *B06B 1/06* (2013.01); *A61N 1/3787* (2013.01)

(58) Field of Classification Search
CPC ........... H02J 50/15; B06B 1/06; A61N 1/3787
USPC .......................................................... 307/104
See application file for complete search history.

(56) References Cited

U.S. PATENT DOCUMENTS 8,784,356 B2 * 7/2014 Sliwa ............... A61B 17/22012 604/22
8,974,366 B1 * 3/2015 Radziemski ....... A61N 1/37217 600/16
2017/0201131 A1 * 7/2017 Vihvelin ................. H02J 50/80
2017/0319858 A1 * 11/2017 Radziemski ....... A61N 1/37223
2018/0226838 A1 * 8/2018 Govindaraj ............. H02J 50/15
2019/0053787 A1 * 2/2019 Stigall ................... G06T 7/0012
2019/0054323 A1 * 2/2019 Stigall ...................... A61B 8/56
2019/0217130 A1 * 7/2019 Boer ...................... A61B 18/04
2019/0313908 A1 * 10/2019 Melodia ............... A61B 5/0031
2021/0196989 A1 * 7/2021 Rinaldi .................. A61N 7/022
(Continued)

FOREIGN PATENT DOCUMENTS

EP 1 771 224 B1 9/2012
EP 3 789 125 A1 3/2021

OTHER PUBLICATIONS

Republique Francaise Institut National De La Propriete Industrielle, Search Report issued in corresponding Application No. FR 22/06419, mailed Feb. 9, 2023.

(Continued)

*Primary Examiner* — Alfonso Perez Borroto
(74) *Attorney, Agent, or Firm* — Stites & Harbison, PLLC; Jeffrey A. Haeberlin

(57) ABSTRACT

An implantable medical device includes a first substrate based on a biocompatible material, wherein the first substrate constitutes a part of a housing of the device and has an external side configured to be put in contact with the biological tissues of a user, wherein the device comprises at least one ultrasonic transducer within a cavity created on an internal side of the first substrate, wherein the transducer is configured so that no layer of air, of gas or of void separates the transducer from the first substrate.

9 Claims, 4 Drawing Sheets

(56) References Cited

U.S. PATENT DOCUMENTS

| | | | | |
|---|---|---|---|---|
| 2022/0131424 | A1* | 4/2022 | Charthad ............. | A61N 1/3787 |
| 2022/0143414 | A1* | 5/2022 | Maharbiz ........... | A61B 5/14539 |
| 2022/0409173 | A1 | 12/2022 | Bihler et al. | |

OTHER PUBLICATIONS

He, Q., et al. MEMS-based ultrasonic transducer as the receiver for wireless power supply of the implantable microdevices, Sensors and Actuators A: Physical, vol. 219, Aug. 26, 2014, pp. 65-72.

* cited by examiner

101

103
101

105
103
101

105
103
107a
107b
107
101

111
105
107b
C
C
101

115
111
115
107a
107b
107
113
101
105

201

203
201

203
201
205

211
203
C
C
201
205

211
203
207a
207
201
205
206

211
209b
207b
203
207
207a 201
211
209a
220
211
209a
207a
203

201
207
205
221
206
211
220
211
209a
207a 213
201
207
205
221
206
211
203'
301
211
220
209a
207a
213
201
207
205
305
221
206

IMPLANTABLE MEDICAL DEVICE AND METHOD TO MANUFACTURE SUCH A DEVICE

TECHNICAL FIELD

The present disclosure generally relates to devices and systems based on ultrasonic transducers, in particular to an implantable medical device that incorporates at least one ultrasonic transducer, and to a process to manufacture such a device.

BACKGROUND ART

An implantable medical device is a device designed for implantation in the body of a patient to monitor and/or treat various types of pathologies. Such a device can comprise one or several sensors, for example to measure at least one physiological parameter, and/or one or several actuators, for example to deliver a treatment or to stimulate an organ.

These elements are generally accommodated in a housing based on a biocompatible material or implantation in the body of the patient.

An implantable medical device usually comprises a non-rechargeable battery to supply power to its various elements. However, this has limitations in terms of life duration and dimensions.

It is advisable to reduce, at least partially, some aspects of known implantable medical devices.

To reduce the dimensions and/or increase the life duration of an implantable medical device, it has been suggested to use a rechargeable battery powered by a wireless energy transfer system, in particular by an ultrasonic wireless energy transfer system.

The present application aims at the advantageous P integration of at least one ultrasonic transducer in an implantable medical device, in particular for applications of ultrasonic wireless energy reloading.

SUMMARY OF INVENTION

To reduce the dimensions and/or increase the life duration of an implantable medical device, an embodiment incorporates the use a rechargeable battery powered by a wireless energy transfer system, in particular by an ultrasonic wireless energy transfer system.

The present application aims at the advantageous integration of at least one ultrasonic transducer in an implantable medical device, in particular for applications of ultrasonic wireless energy reloading.

An embodiment incorporates an implantable medical device comprising a first substrate based on a biocompatible material, wherein the first substrate constitutes a part of a housing of the device and has an external side configured to be put in contact with the biological tissues of a user, wherein the device comprises at least one ultrasonic transducer within a cavity created on an internal side of the first substrate, wherein the transducer is configured so that no layer of air, of gas or of void separates the transducer from the first substrate.

According to an embodiment, the cavity is a non-through cavity in the first substrate on the internal side of the first substrate.

According to an embodiment, the first substrate is based on an electrically isolating material, for example on sapphire.

According to an embodiment, the device additionally comprises a second substrate bonded onto the first substrate on the internal side of the first substrate, wherein the cavity is a cavity all through the second substrate until the first substrate.

According to an embodiment, the first substrate is made of metal, for example made of titanium.

According to an embodiment, the second substrate is based on an electrically isolating material.

According to an embodiment, the second substrate comprises a printed circuit.

According to an embodiment, the device additionally comprises, over the upper side of the first substrate, interconnecting metal elements respectively connected to first and second electrodes of the transducer.

According to an embodiment, the device additionally comprises, over the upper side of the first substrate, a control electronic circuit connected to the first and second electrodes of the transducer via said interconnecting metal elements.

According to an embodiment, the device additionally comprises a battery over the upper side of the first substrate and connected to the control electronic circuit.

According to an embodiment, the battery lies in a cavity on the internal side of the first substrate inside the housing.

According to an embodiment, the control electronic circuit is configured to convert an electrical power from the ultrasonic transducer into an electric signal to reload the battery and/or to supply power to electronic elements of the device.

Another embodiment incorporates a method to manufacture a device as described above, comprising a step of manufacturing of the cavity, following by a step of transfer and fixation of the transducer into the cavity.

According to an embodiment, the cavity is manufactured by laser ablation.

BRIEF DESCRIPTION OF DRAWINGS

The foregoing features and advantages, as well as others, will be described in detail in the following description of specific embodiments given by way of illustration and not limitation with reference to the accompanying drawings, in which.

DESCRIPTION OF EMBODIMENTS

Figures 1A, 1B, 1C, 1D, 1E, 1F:
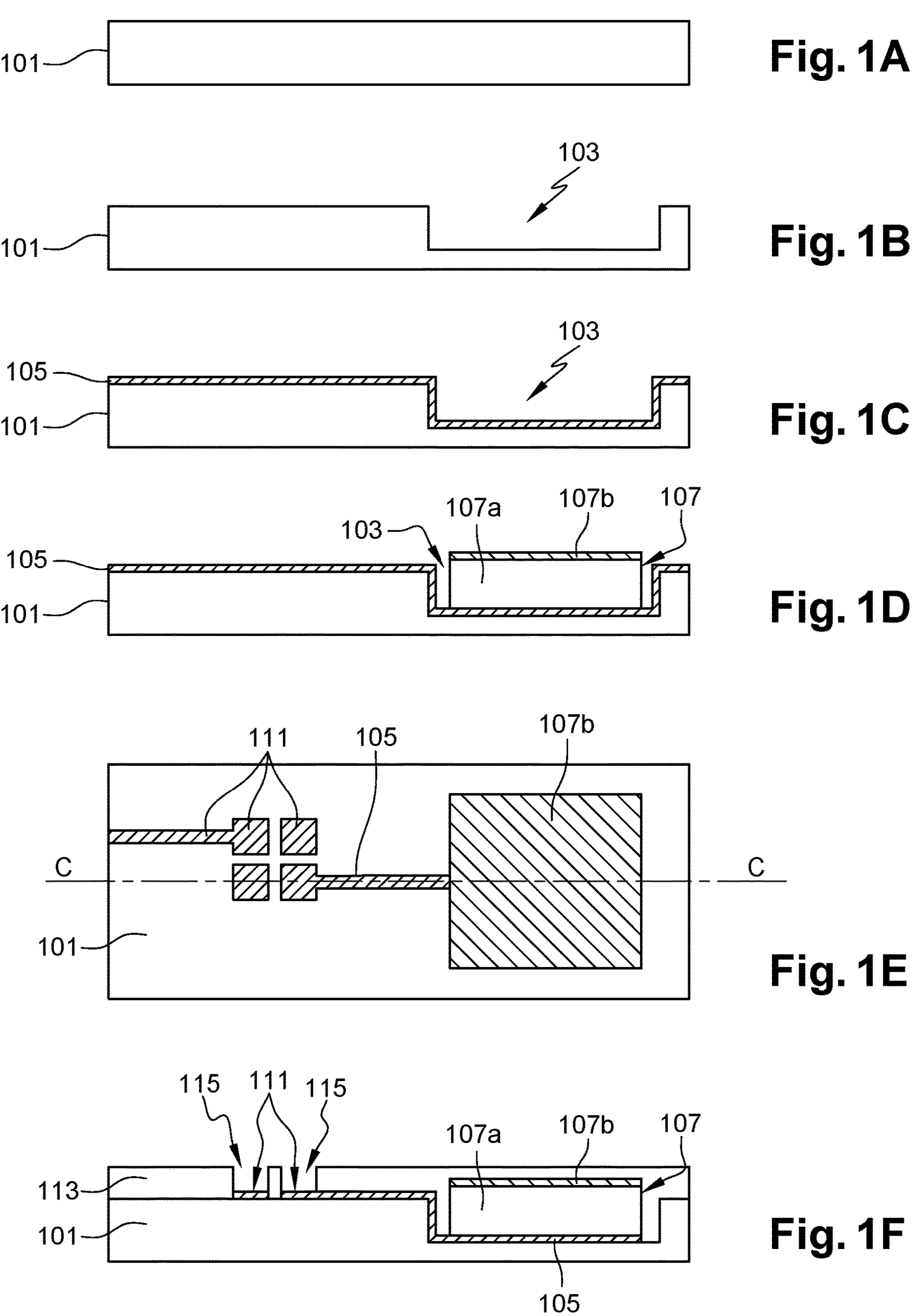
FIG. 1A, FIG. 1B, FIG. 1C, FIG. 1D, FIG. 1E, FIG. 1F, FIG. 1G, FIG. 1H, FIG. 1I and FIG. 1J schematically and partially illustrate successive steps of an embodiment of a method to manufacture an implantable medical device comprising an ultrasonic transducer.

Like features have been designated by like references in the various figures. In particular, the structural and/or functional features that are common among the various embodiments may have the same references and may dispose identical structural, dimensional and material properties.

For the sake of clarity, only the operations and elements that are useful for an understanding of the embodiments described herein have been illustrated and described in detail. In particular, only the integration of at least one ultrasonic transducer in an implantable medical device has been described. The manufacture of the ultrasonic transducers has not been described, since the described embodiments are compatible with all or most of the known ultrasonic transducers. In addition, the manufacture and the integration of the other elements of the implantable medical device (battery, sensors, actuators, control and/or treatment electronic circuits, etc.) has not been described, since the described embodiments are compatible with the usual manufactures and integrations of these elements or since a person skilled in the art will be able to manufacture and integrate these elements starting from the specifications of the present disclosure.

Unless indicated otherwise, when reference is made to two elements connected together, this signifies a direct connection without any intermediate elements other than conductors, and when reference is made to two elements coupled together, this signifies that these two elements can be connected or they can be coupled via one or more other elements.

In the following disclosure, unless indicated otherwise, when reference is made to absolute positional qualifiers, such as the terms “front”, “back”, “top”, “bottom”, “left”, “right”, etc., or to relative positional qualifiers, such as the terms “above”, “below”, “higher”, “lower”, etc., or to qualifiers of orientation, such as “horizontal”, “vertical”, etc., reference is made to the orientation shown in the figures.

Unless specified otherwise, the expressions “around”, “approximately”, “substantially” and “in the order of” signify within 10%, and preferably within 5%.

The FIG. 1A to 1J schematically and partially illustrate successive steps of an example of a method to manufacture an implantable medical device comprising at least one ultrasonic transducer according to an embodiment. The transducer is configured, for example, for use in applications for ultrasonic wireless energy transfer, for example to reload a battery (not illustrated on the figures) of the device. To do so, an ultrasonic transducer, external to the implantable medical device and powered by an external power source, emits ultrasounds towards the ultrasonic transducer of the implantable medical device. The transducer of the implantable medical device converts the received ultrasounds into electrical energy to reload the battery of the implantable medical device. Thus, an ultrasonic wireless electric energy transfer is made from the external power source to the battery of the implantable medical device. As a variant or in a complementary manner, the at least one ultrasonic transducer of the device can be used for applications of communication with an external device or for sensing or measurement applications.

FIG. 1A is a cross-section of a biocompatible substrate 101, for example an electrically isolating substrate. The substrate 101, for example, is made of sapphire. As a variant (not illustrated in the figures), the substrate can comprise a support based on a material that may not be biocompatible, coated with an external layer or coating based on a biocompatible material, for example a biocompatible polymer material, for example parylene.

The substrate 101 is configured, for example, to constitute a part of an encapsulation housing of the implantable medical device. In this example, the upper side of the substrate 101 is an internal face of the housing, configured to receive internal elements of the medical device, in particular at least one ultrasonic transducer. The lower side of the substrate 101, for example, is an external side of the housing, configured to be put in contact with biological tissues of a patient. The substrate 101 has, for example, the shape of a plate, for example rectangular, with a substantially homogeneous thickness. The thickness of the substrate 101 is, for example, between 500 μm and 3 mm. The lateral dimensions of the plate (that match the lateral dimensions of the housing) are, for example, between 1 and 10 centimeters. The design of a single implantable medical device is (partly) illustrated in the FIGS. 1A to 1J. Practically, several devices can be manufactured in parallel and simultaneously from the same substrate 101 with bigger lateral dimensions, and then be cut apart at a cutting stage of the substrate 101.

FIG. 1B is a cross-section that illustrates the structure after a stage of manufacture of a cavity 103 located in a part of the thickness of the substrate 101. The cavity 103 extends vertically from the upper side of the substrate 101 across only a part of the thickness of the substrate. The depth of the cavity 103, for example, is between 0.1 and 2 mm. The cavity 103 is configured to receive an ultrasonic transducer of the device. The lateral dimensions of the cavity 103, for example, are between 0.2 and 2 cm, for example between 0.5 and 1 cm. The cavity 103 is, for example, manufactured by laser ablation. From above, the cavity 103 has, for example, a rectangular shape.

FIG. 1C is a cross-section that illustrates the structure after a stage of deposition of a metal layer 105 onto the upper side of the substrate 101. The metal layer 105 extends, for example, continuously and with a substantially homogeneous thickness over the whole upper surface of the substrate 101, which means on the sides and the bottom of the cavity 103, and over the upper side of the substrate 101 outside the cavity 103. For example, the metal layer 105 is in contact, thanks to its lower side, with the upper side of the substrate 101. For example, the metal layer 105 is based on gold, silver or copper. The metal layer 105 can comprise a stack (not illustrated in the figures) of several layers of various metals. The metal layer 105 can comprise, for example, an adhesion layer, for example based on nickel, in contact with the substrate 101, coated with a layer based on another metal, for example gold, silver or copper. The metal layer 105 is deposited, for example, by a phase vapor deposition process (PVD). The thickness of the metal layer 105 is, for example, between 0.1 and 1 μm.

FIG. 1D is a cross-section that illustrates the structure after a stage of transfer and fixation of an ultrasonic transducer 107 into the cavity 103. The transducer 107, for example, is a piezoelectric transducer. The transducer, for example, comprises a layer or pellet 107*a* made of a piezoelectric material, and an upper conducting electrode 107*b*, for example based on metal, on and in contact with the upper side of the piezoelectric layer 107*a*. The piezoelectric layer 107 is, for example, based on a piezoelectric ceramic, for example a PZT ceramic (lead zirconate titanate). The electrode 107*b* extends, for example, over substantially all the upper surface of the piezoelectric layer 107*a*. In this example, the piezoelectric layer is bonded on and electrically connected to the upper side of the metallic layer 105, at the bottom of the cavity 103, for example thanks to a glue, for example an electrically conducting glue. In this case, the part of the metallic layer 105 located at the bottom of the cavity 103 constitutes the lower electrode of the transducer 107. The transducer 107, as an example, has lateral dimensions substantially identical to those of the cavity 103, for example lower than ten percent of the lateral dimensions of the cavity 103. Thus, the transducer 107 occupies substantially all the surface of the cavity 103. The thickness of the transducer 107 is, for example, substantially equal to the depth of the cavity 103, for example equal more or less 20 percent, preferably more or less 10 percent, to the depth of the cavity 103. The transducer 107 can be taken off a support and positioned into the cavity 103 thank to a tool for pick and place. There could be one or several intermediate layers (not illustrated in the figures) for reflection (acoustic mirror) or absorption of acoustic waves, for example electrically conducting, between the upper side of the piezoelectric material 107*a* and the upper electrode 107*b*.

It shall be noted that the described embodiments are not limited to the example as described above, where the transducer 107 is a piezoelectric transducer. More generally, the modes for carrying out the invention can be adapted to suit any type of ultrasonic transducer, for example capacitive ultrasound transducers with membrane (CMUT), piezoelectric ultrasound transducers with membrane (PMUT), etc. There can be one or several intermediate layers for acoustic impedance matching and/or output work matching, for example electrically conducting, between the lower side of the transducer and the metallic layer 105. In any case, according to an embodiment of the FIGS. 1A to 1J, no layer of air, gas or void separates the lower side of the transducer 107 from the upper side of the substrate 101 at the bottom of the cavity 103. In other words, the transducer 107 is mechanically in contact with the upper side of the substrate 101, or is separated from the upper side of the substrate 101 only by one or several solid materials. More specifically, in the example illustrated by the figures, no layer of air, gas or void separates the lower side of the piezoelectric layer 107*a* of the transducer 107 from the upper side of the substrate 101 at the bottom of the cavity 103. In other words, the piezoelectric layer 107*a* of the transducer is mechanically in contact with the upper side of the substrate 101, or is separated from the upper side of the substrate 101 only by one or several solid materials. Hence, advantageously, the acoustic power received from the lower side of the substrate 101 from an external device is effectively transmitted with little loss to the transducer 107. Conversely, in case of emission of ultrasonic waves by the transducer 107, the acoustic power from the transducer is effectively transmitted with little loss out of the device through the substrate 101.

In the embodiment of the FIGS. 1A to 1J, a localized thinning of the substrate 101 in line with the transducer 107 (cavity 103) advantageously reduces the global dimensions of the device and allows a better transmission of acoustic waves between the transducer and the outside of the housing. Preferably, the thickness of the substrate 101 at the bottom of the cavity 103 is selected so that it improves the acoustic coupling between the transducer 107 and the outside of the housing. The thickness of the substrate 101 at the bottom of the cavity 103, for example, is between 0.2 and 1 mm. Fixing the transducer 107 in the cavity 103 maintains the housing rigid at the location of the cavity.

FIG. 1E is a view from above that illustrates the structure after a stage of localized removal of the metal layer 105 on the upper side of the substrate 101, for example by photolithography and etching or laser ablation, in order to delimit conducting paths and connector surfaces 111 for interconnection of the device. It shall be noted that the cross-sections of the FIGS. 1A to 1J are made in the cutting plane C-C of FIG. 1E.

As a variant, the steps of the FIGS. 1D (transfer and fixation of the transducer 107 into the cavity 103) and 1E (etching of the interconnection elements 111 in the metal layer 105) can be made the other way around, which means that the steps of FIG. 1E can be implemented before the steps of FIG. 1D.

FIG. 1F is a cross-section that illustrates a structure resulting from a step of deposition of a passivation electrically insulating layer 113 on the upper side of the structure of FIG. 1E, followed by a step of formation of localized apertures 115 in the layer 113.

The layer 113 is, for example, a layer based on a polymer material, for example a polyimide. The layer 113 is, for example, first deposited over the whole upper surface of the structure of FIG. 1E. The thickness of the layer 113 is, for example, between 10 and 100 μm.

Then, the layer 113 is locally removed, for example by laser ablation, in order to create through apertures 115 vertically aligned with metal connection surfaces 111 previously delimited in the metal layer 105 (FIG. 1D). The apertures 115 reach the upper side of the metal connection surfaces 111 in order to allow later reconnection on the connection surfaces 111. At least one localized contacting aperture 115 (not visible in FIG. 1F) can additionally be created in line with the upper electrode 107*b* of the transducer 107, in order to reconnect an electrical current to the electrode 107*b*.

Figure 1G:
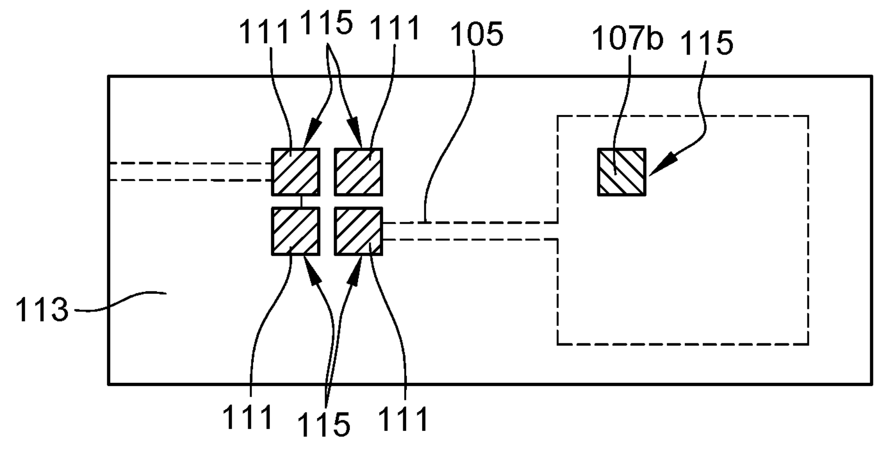

FIG. 1G is a view from below of the structure of FIG. 1F. In this example, four localized apertures 115 have been created in line respectively of four connection metallic surfaces 111 deposited on the upper surface of the substrate 101. One of these metallic surfaces 111 is electrically connected to the lower electrode of the transducer 107 through a conducting path created in the metallic level 105. The metallic surfaces 111 are, for example, configured to connect to pads constituting an electronic circuit to control the transducer, for example an electronic circuit integrated in and on a semiconductor substrate, for example a CMOS circuit. In this example, an additional localized aperture 115 is created in line with the upper electrode 107*b* of the transducer.

Figure 1H:
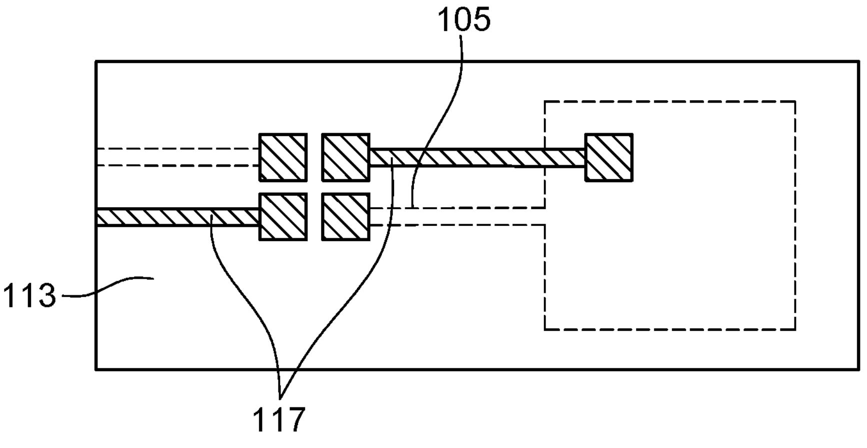

The FIG. 1H illustrates a structure resulting from a manufacturing step of interconnection metallic elements 117 on the upper side of the structure of FIG. 1G. For example, a metal layer continuously extending over the whole upper surface of the structure can be deposited. This layer is then locally removed, for example by photolithography and etching, to manufacture the interconnection elements 117. For example, among the interconnection elements 117, a conducting path electrically connects the part of the upper electrode 107*b* of the transducer that was uncovered at the previous stage to one of the metallic surfaces 111 also uncovered at the previous stage.

Figure 1I:
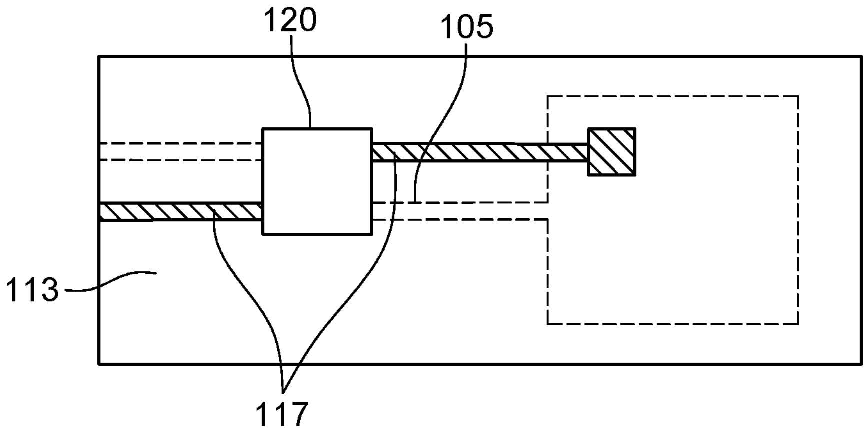
Figure 1J:
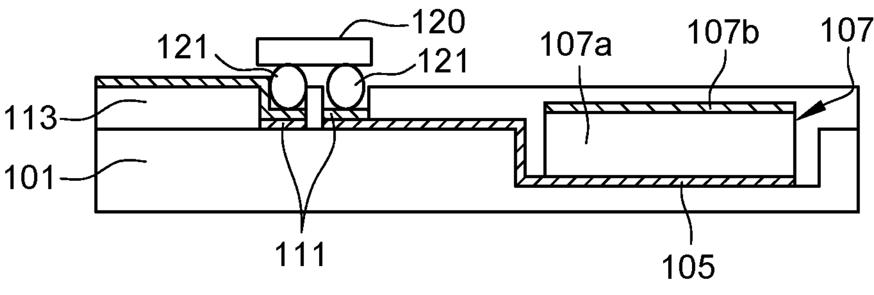

The FIGS. 1I and 1J are respectively a view from above and a cross-section of the structure resulting from a transfer step of an interconnection metallic element 120 onto the upper side of the structure of FIG. 1H.

In this example, the control electronic circuit 120 is a circuit integrated in and on a semiconductor substrate, for example a silicon substrate. The circuit 120 comprises connection pads 121, electrically connected, for example by soldering or brazing, to corresponding metallic surfaces for connection of the device, which are, for example, formed in the metallic level 105/111 and/or in the metallic level 117. In this example, the control electronic circuit comprises two pads respectively connected to the lower electrode and to the upper electrode of the transducer 107. The control electronic circuit 120 can additionally comprise several pads connected to power supply terminals and/or input/output terminals for control signals and/or for data of the device. The control electronic circuit 120, as a variant, can comprise several semiconductor chips and/or several interconnected discrete electronic elements and connected to the ultrasonic transducer 107 through interconnection elements in the metallic level 105/111 and/or in the metallic level 117. The metallic levels 105/111 and 117 can be used to interconnect other elements (not illustrated) of the medical device. Practically, the number of interconnection metallic levels in the upper side of the substrate 101 can be different from two, for example equal to 1 or more than 2.

Furthermore, although not illustrated in the figures, a battery can be transferred onto the upper side of the substrate 101 and electrically connected to interconnection elements on the upper side of the substrate 101. The battery is, for example, electrically connected to the electronic control circuit 120. The electronic circuit 120, for example, comprises a power converter circuit configured to reload the battery thanks to electric power generated at the terminals of the ultrasonic transducer under the action of an acoustic wave from an external device.

To reduce dimensions, the battery can be partly or totally accommodated in a cavity previously created in the substrate 101, for example a cavity similar to the cavity 103 but with dimensions suitable to those of the battery.

After these steps, an upper cover (not illustrated in the figures) of the housing of the device, preferably in a biocompatible material, for example based on the same material as the substrate 101, can be transferred onto the upper side of the structure, in order to tightly encapsulate the internal elements of the device. As an example, the upper cover is soldered to the lower part of the housing made of the substrate 101, for example by laser soldering. As an example, the housing constituted by the substrate 101 and the upper cover tightly encapsules the transducer 107, the electronic circuit 120 and the battery of the device.

The FIG. 2A to 2H schematically and partially illustrate successive steps of an example of another embodiment of a method to manufacture an implantable medical device comprising at least one ultrasonic transducer.

Figures 2A, 2B, 2C, 2D, 2E:
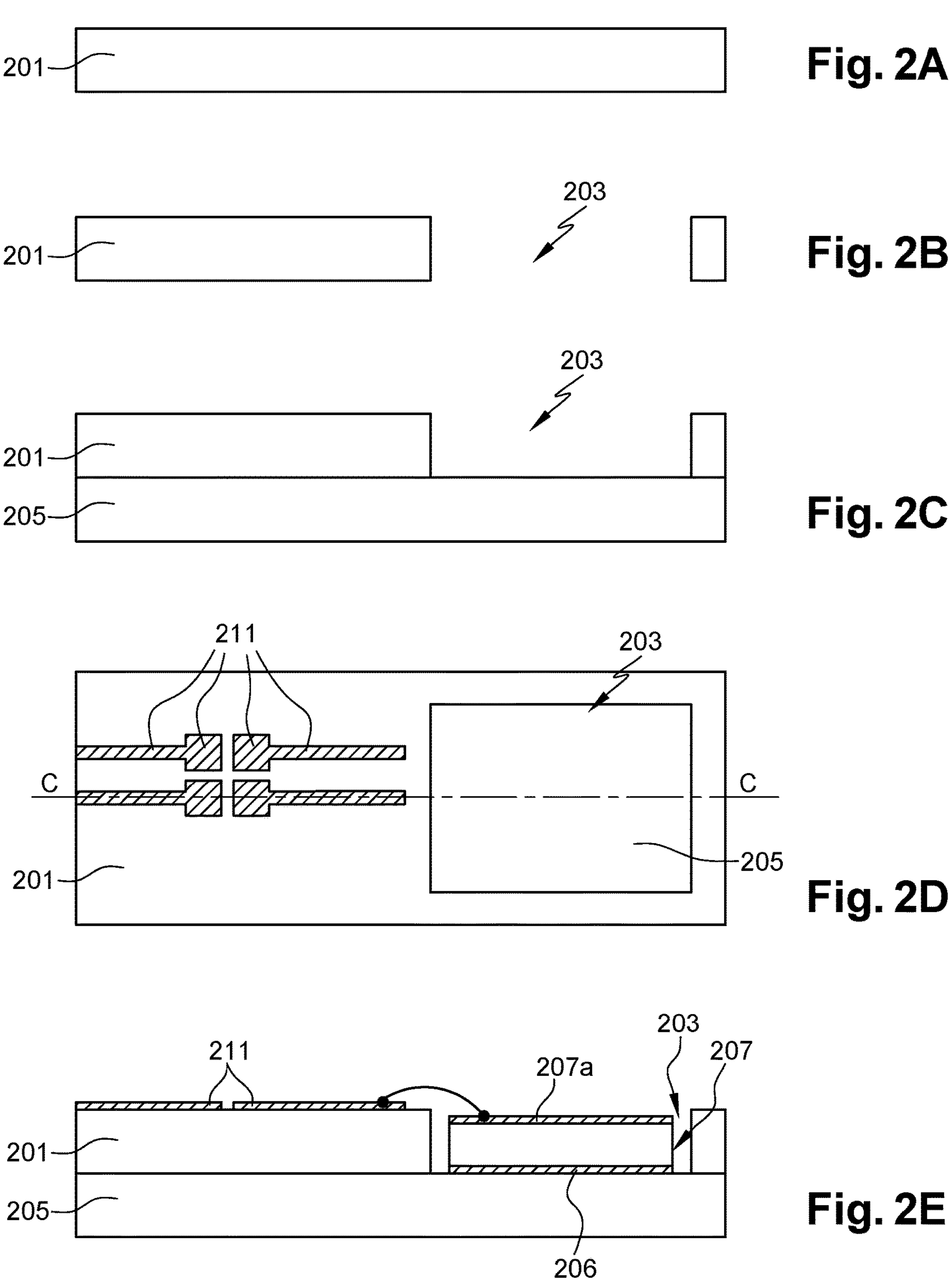
FIG. 2A, FIG. 2B, FIG. 2C, FIG. 2D, FIG. 2E, FIG. 2F, FIG. 2G and FIG. 2H schematically and partially illustrate successive steps of an example of another embodiment of a method to manufacture an implantable medical device comprising an ultrasonic transducer.

FIG. 2A is a cross-section of a substrate 201, initially an electrically isolating material. The thickness of the substrate 201 is, for example, between 0.2 and 3 mm.

FIG. 2B is a cross-section that illustrates the structure after a stage of manufacture of a localized cavity 203 that extends all through the substrate 201. The aperture 203 constitutes an accommodation designed to receive an ultrasonic transducer of the device. The lateral dimensions of the aperture 203, for example, are between 0.2 and 2 cm, for example between 0.5 and 1 cm. The aperture 203 is, for example, manufactured by laser ablation. From above, the aperture 203 has, for example, a rectangular shape.

FIG. 2C is a cross-section that illustrates the structure after a stage of fixation of the substrate 201, by its lower side, onto the upper side of a second substrate 205, for example made of a biocompatible material. The substrate 205, for example, is a metallic substrate. As an example, the substrate 205 is made of titanium. The metal layer 205 extends, for example, continuously and with a substantially homogeneous thickness over the whole lower surface of the substrate 201. In particular, the substrate 205 closes the lower side of the aperture 203. Thus, the aperture 203 constitutes, in the stack that comprises the substrates 201 and 205, a cavity designed to receive an ultrasonic transducer of the medical device. The fixing of the substrate 201 onto the substrate 205, for example, is made by bonding. An intermediate layer (not illustrated) of a bonding material, for example, is deposited at the interface between the two substrates. The thickness of the substrate 201 is, for example, between 0.2 and 1 mm.

The substrate 205 is configured, for example, to constitute a part of an encapsulation housing of the implantable medical device. In this example, the upper side of the stack 205-201 corresponds with an internal face of the housing, configured to receive internal elements of the medical device, in particular at least one ultrasonic transducer. The lower side of the substrate 205, for example, is an external side of the housing, configured to be put in contact with biological tissues of a patient. The stack 205-201 has, for example, the global shape of a plate, for example rectangular. The lateral dimensions of the plate (that match the lateral dimensions of the housing) are, for example, between 1 and 10 centimeters. The design of a single implantable medical device is (partly) illustrated in the FIGS. 2A to 2H.

FIG. 2D is a view from above that illustrates a structure resulting from a manufacturing step of interconnection metallic elements 211 on the upper side of the structure of FIG. 2C, and more specifically, on the upper side of the substrate 201. It shall be noted that the cross-sections of the FIGS. 2A to 2H are made in the cutting plane C-C of FIG. 2D.

For example, a metal layer continuously extending over the whole upper surface of the structure can be deposited. This layer is then locally removed, for example by photolithography and etching, to manufacture the interconnection elements 211. More generally, at this stage, at least one level of printed circuits can be created on the upper side of the substrate 201. As a variant, a printed circuit board, for example flexible, can be transferred and fixed onto the upper side of the substrate 201 next to the cavity 203. The substrate 201 can be replaced, as a variant, by a rigid printed circuit board. As a variant, the steps of the FIG. 2D can be implemented before the step of FIG. 2C, before or after the step of FIG. 2B.

FIG. 2E is a cross-section that illustrates the structure after a stage of transfer and fixation of an ultrasonic transducer 207 into the cavity 203.

Figures 2F, 2G, 2H, 3:
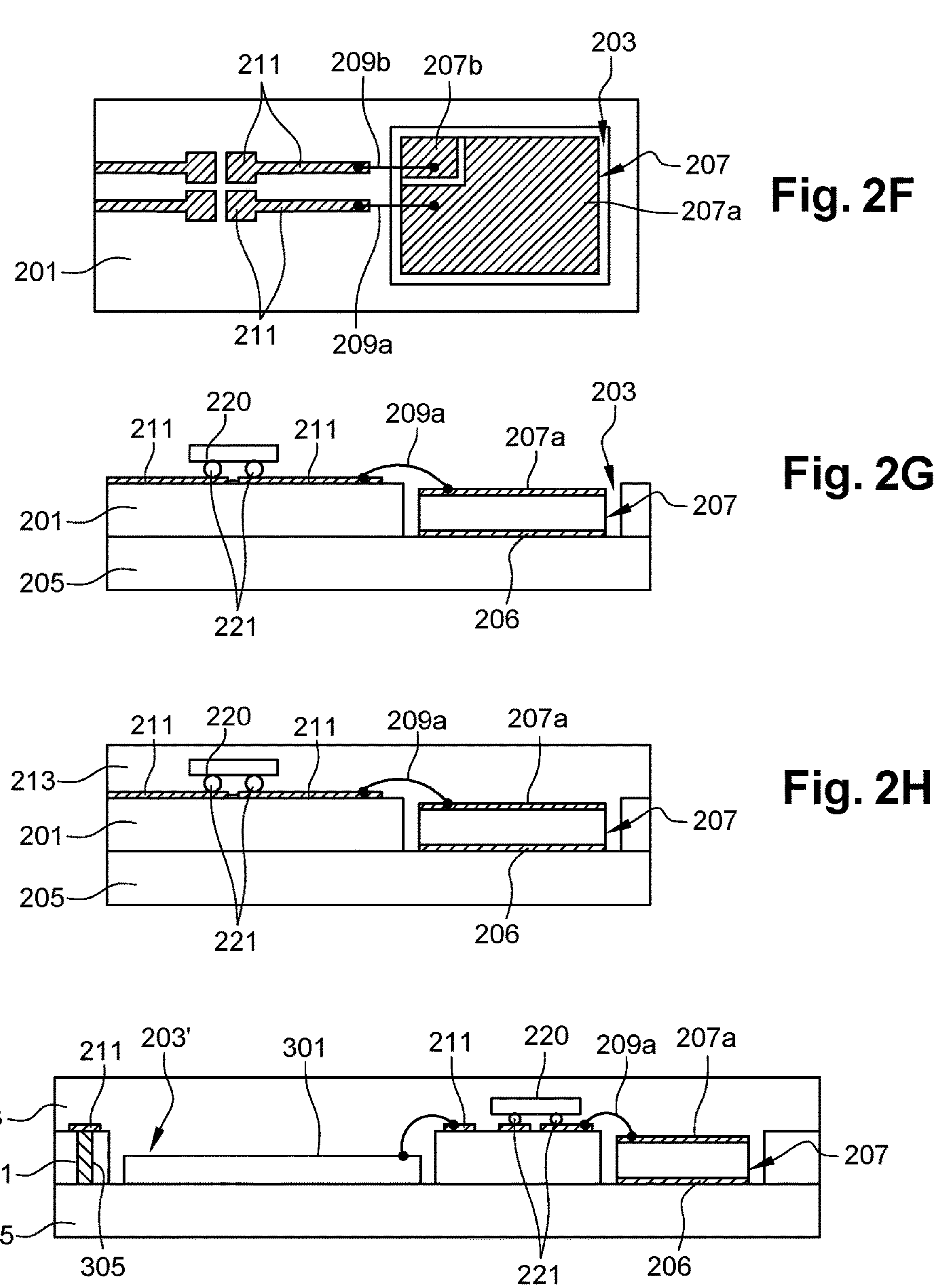
FIG. 3 schematically and partially illustrates a variant of the process according to FIGS. 2A to 2H.

FIG. 2F is a view from below of the structure of FIG. 2E.

The transducer 207, for example, is a piezoelectric transducer. In this example, the transducer comprises two electrodes 207*a* and 207*b* that were transferred onto its upper side. More specifically, in this example, the electrode 207*a* is the upper electrode of the transducer and occupies most of the upper surface of the transducer. The electrode 207*b* brings the electric contact from the lower side of the transducer up to the upper side. A metallic electrode 206, as an example, extends over the lower side of the transducer, for example over the whole lower surface of the transducer or over the most part of the lower surface of the transducer. The electrodes 206 and 207*a* are, for example, in contact with respectively the lower side and the upper side of a piezoelectric layer of the transducer. There could be one or several intermediate layers (not illustrated in the figures) for reflection (acoustic mirror) or absorption of acoustic waves, for example electrically conducting, between the upper side of the piezoelectric material and the upper electrode 207*a*. The electrode 207*b* can be connected to the electrode 206 through an electrically conducting via (not illustrated on the figures) vertically across the transducer or thanks to a metal path (not visible in the figures) extending on an edge of the transducer. As a variant, a metal plating can be created at the bottom of the cavity 203 before the transfer of the transducer, which makes it possible to restore the contact on the lower electrode of the transducer and bring this contact to the upper side of the structure 201 through conducting paths. As described above, the piezoelectric layer is, for example, based on a piezoelectric ceramic, for example a PZT ceramic (lead zirconate titanate).

For example, the transducer 207 is fixed thanks to its lower side, to the upper side of the substrate 205 at the bottom of the cavity 203. The fixing is made, for example, thanks to a glue, not visible on the figure. The glue can be electrically conducting, for example if it is desirable to apply the voltage from the substrate 205 in contact with the biological tissues to the lower electrode of the transducer. As a variant, the glue can be electrically isolating.

The transducer 207, as an example, has lateral dimensions substantially identical to those of the cavity 203, for example lower than ten percent of the lateral dimensions of the cavity 203. Thus, the transducer 207 occupies substantially all the surface of the cavity 203. The thickness of the transducer 207 is, for example, substantially equal to the depth of the cavity 203, for example equal more or less 20 percent, preferably more or less 10 percent, to the depth of the cavity 203 (which matches, in this example, the thickness of the substrate 201). The transducer 207 can be taken off a support and positioned into the cavity 203 thank to a tool for pick and place.

It shall be noted that the described embodiments are not limited to the example as described above, where the transducer 207 is a piezoelectric transducer. More generally, the modes for carrying out the invention can be adapted to suit any type of ultrasonic transducer, for example capacitive ultrasound transducers with membrane (CMUT), piezoelectric ultrasound transducers with membrane (PMUT), etc. There can be one or several intermediate layers for acoustic impedance matching and/or output work matching, for example electrically conducting, between the lower side of the transducer and the substrate 205. In any case, according to an embodiment of the FIGS. 2A to 2H, no layer of air, gas or void separates the lower side of the transducer 207 from the upper side of the substrate 205 at the bottom of the cavity 203. In other words, the transducer 207 is mechanically in contact with the upper side of the substrate 205, or is separated from the upper side of the substrate 205 only by one or several solid materials. This makes it advantageously possible to favor the transfers of acoustic energy between the transducer and the outside through the substrate 205. More specifically, in the example illustrated by the figures, no layer of air, gas or void separates the lower side of the piezoelectric layer of the transducer 207 from the upper side of the substrate 205 at the bottom of the cavity. In other words, the piezoelectric layer of the transducer 207 is mechanically in contact with the upper side of the substrate 205, or is separated from the upper side of the substrate 205 only by one or several solid materials.

Preferably, the thickness of the substrate 201 is selected so that it improves the acoustic coupling between the transducer 207 and the outside of the housing.

In this example, the electrodes 207*a* and 207*b* of the transducer are electrically connected respectively to two metallic connection surfaces 211 created on the upper side of the substrate 201 (FIG. 2D) thanks to electrically conducting wires 209*a*, 209*b*, for example metallic wires, for example based on gold or copper.

FIG. 2G is a cross-section of the structure resulting from a transfer step of an interconnection metallic element 220 onto the upper side of the structure of the FIGS. 2E and 2F.

In this example, the control electronic circuit 220 is an integrated circuit in and on a semiconductor substrate, for example a silicon substrate. The circuit 220 comprises electrically connected pads 221, for example connected by soldering, to corresponding metallic surfaces 211 of the device. In this example, the control electronic circuit comprises two pads respectively connected to the lower electrode and to the upper electrode of the transducer 207. The control electronic circuit 220 can additionally comprise several pads connected to power supply terminals and/or input/output terminals for control signals and/or for data of the device. The control electronic circuit 220, as a variant, can comprise several semiconductor chips and/or several interconnected discrete electronic elements and connected to the ultrasonic transducer 207 through interconnection elements in the upper side of the substrate 201.

Although not illustrated in the figures, a battery can be transferred onto the upper side of the substrate 201 and electrically connected to interconnection elements on the upper side of the substrate 201. The battery is, for example, electrically connected to the electronic control circuit 220.

FIG. 2H is a cross-section that illustrates a structure resulting from a facultative step of deposition of a passivation electrically insulating layer 213 on the upper side of the structure of FIG. 2H. The layer 213 is, for example, based on a polymer material. As an example, the layer 213 extends continuously over the whole upper surface of the structure and, in particular, covers the electronic circuit 220 and the ultrasonic transducer 207. The layer 213 can be removed, as a variant, from over the transducer 207 not to alter the acoustic characteristics of the device. Similarly as above, after these steps, an upper cover (not illustrated in the figures) of the housing of the device, preferably in a biocompatible material, for example based on the same material as the substrate 205, can be transferred onto the upper side of the structure, in order to tightly encapsulate the internal elements of the device.

FIG. 3 schematically and partially illustrates a variant of the device of FIG. 2H.

The device of FIG. 3 is different from the device of FIG. 2H, mainly in that it comprises a battery 301 accommodated in a cavity 203' similar to the cavity 203 (a through aperture across the substrate 201) but with lateral dimensions suitable to the dimensions of the battery. As an example, from above, the battery has a surface of at least 1 $cm^2$. The battery 301 is electrically connected to interconnected elements on the upper side of the substrate 201. The battery is, for example, electrically connected to the electronic control circuit 220.

In the illustrated example, the battery 301 comprises an upper electrode electrically connected to the metallic connection surface 211 on the upper side of the substrate 201 thanks to a conducting wire 303, for example a metallic wire, for example based on copper, and a lower electrode in mechanical and electrical contact with the upper side of the metallic substrate 205. In this example, the metallic substrate 205 is used as a ground plane. An electrically conducting via 305 that vertically crosses the substrate 201 electrically connects the substrate 205 to a metallic connection element 211 on the upper side of the substrate 201.

It shall be noted that, similarly, in the example of the FIGS. 2A to 2H, it is possible to electrically connect a lower electrode of the transducer 207 to a metallic interconnection element 211 through the metallic substrate 205 and an electrically conducting via that vertically crosses the substrate 201 all through.

As a variant, in the example of FIG. 3, the two electrodes of the battery 301 are brought to the upper side and are connected to metallic connection elements 211 on the upper side of the substrate 201 through respectively two conducting wires.

An advantage of the described embodiments is a compact and performing integration of ultrasonic transducers in an implantable medical device, for example, for an ultrasonic wireless electrical energy transfer to the implantable medical device.

Various embodiments and variants have been described. Those skilled in the art will understand that certain features of these embodiments can be combined and other variants will readily occur to those skilled in the art.

Finally, the practical implementation of the embodiments and variants described herein is within the capabilities of those skilled in the art based on the functional description provided hereabove.

What is claimed is:

1. An implantable medical device comprising:

a first substrate based on a biocompatible material, wherein the first substrate constitutes a part of an encapsulation housing of the device and has an external side, defining an external side of the encapsulation housing, configured to be put in contact with the biological tissues of a user, and an internal side opposite to the external side; and at least one ultrasonic transducer within a non-through cavity formed in the first substrate on the internal side of the first substrate, wherein the ultrasonic transducer comprises a layer of a piezoelectric material distinct from the first substrate, the ultrasonic transducer being configured so that no layer of air, of gas or of void separates from the internal side of the first substrate.

2. The device according to claim 1, wherein the first substrate is based on an electrically isolating material, for example on sapphire.

3. The device according to claim 1, additionally comprising, over the internal side of the first substrate, interconnecting metal elements respectively connected to first and second electrodes of the transducer.

4. The device according to claim 3, additionally comprising, over the internal side of the first substrate, a control electronic circuit connected to the first and second electrodes of the transducer via said interconnecting metal elements.

5. The device according to claim 1, wherein the piezoelectric layer of the transducer is based on a piezoelectric ceramic, for example on PZT.

6. The device according to claim 1, wherein the housing additionally comprises an upper cover based on the same material as the first substrate, for example soldered to the first substrate, that hermetically encapsulates the ultrasonic transducer.

7. A method to manufacture the device according to claim 1, comprising a step of manufacturing said cavity, following by a step of transfer and fixation of the transducer into the cavity.

8. The method according to claim 7, wherein the cavity is manufactured by laser ablation.

9. The device according to claim 1, wherein the ultrasonic transducer comprises a lower metallic electrode disposed on and in contact with the internal side of the first substrate.

* * * * *